United States Patent [19]

Yamada et al.

[11] Patent Number: 4,668,776

[45] Date of Patent: May 26, 1987

[54] PROTECTED DES-N-METHYLERYTHROMYCIN DERIVATIVE

[75] Inventors: Toshiro Yamada, Fujisawa; Hiroshi Fujisawa, Yokohama; Kuniaki Goto, Tokyo; Shigeo Morimoto, Yoshikawamachi; Takashi Adachi, Washimiyamachi; Yoshiaki Watanabe, Kodaira, all of Japan

[73] Assignees: Nippon Zeon Co. Ltd.; Taisho Pharmaceutical Co. Ltd., both of Japan

[21] Appl. No.: 846,520

[22] Filed: Mar. 31, 1986

[30] Foreign Application Priority Data

Apr. 3, 1985 [JP] Japan ................................. 60-69192

[51] Int. Cl.$^4$ ............................................. C07H 17/08
[52] U.S. Cl. ........................................ 536/7.4; 536/7.2
[58] Field of Search ................................. 536/7.4, 7.2

[56] References Cited

U.S. PATENT DOCUMENTS

| | | | |
|---|---|---|---|
| 3,869,444 | 3/1975 | Freiberg ................................. | 536/7.4 |
| 3,923,784 | 12/1975 | Kierstead et al. ..................... | 536/7.4 |
| 4,331,803 | 5/1982 | Watanabe et al. .................... | 536/7.2 |
| 4,349,545 | 9/1982 | d'Ambrieres et al. ................ | 536/7.4 |
| 4,496,717 | 1/1985 | Adachi et al. ......................... | 536/7.2 |

FOREIGN PATENT DOCUMENTS 80819 6/1983 European Pat. Off. ............. 536/7.2

OTHER PUBLICATIONS

Journal of Organic Chemistry, vol. 31, p. 3446 (1966).

*Primary Examiner*—Johnnie R. Brown
*Assistant Examiner*—Elli Peselev
*Attorney, Agent, or Firm*—Lowe, Price, LeBlanc, Becker & Shur

[57] ABSTRACT

There is disclosed a novel protected des-N-methylerythromycin derivative, in which 2', 3' and 9-positions are protected with new substituents that can provide stabler derivative and can be eliminated in a single reaction under neutral condition.

5 Claims, No Drawings

PROTECTED DES-N-METHYLERYTHROMYCIN DERIVATIVE

BACKGROUND OF THE INVENTION

The present invention relates to a protected des-N-methylerythromycin derivative adapted for use as an intermediate for synthesis of chemically modified erythromycin derivatives.

Erythromycin A and erythromycin B are macrolide antibiotics obtainable through culture of streptomyces erythreus, and are represented by the following formula:

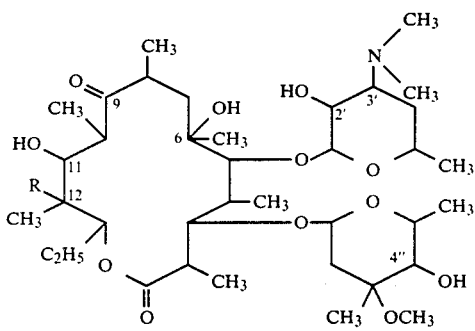

wherein
R=OH for erythromycin A; and
R=H for erythromycin B.

There have recently been made various attempts to improve the pharmaceutical effects through chemical modification of such erythromycins, such as methylation of the hydroxyl group in the 6- or 11-position of erythronolide or the hydroxyl group in the 4"-position of cladinose, as disclosed in the U.S. Pat. No. 4,331,803, E. Pat. No. 80,819 and U.S. Pat. No. 4,496,717.

In such chemical modification, in order to improve the selectivity of the reaction, it is necessary to protect the hydroxyl group in 2'-position or the amino group in 3-position, which are chemically active, as disclosed in the Japanese Patent Application Kokai Publication No. 58-92692.

However carbobenzoxy chloride (Z-cl) which has been widely employed as protecting agent is associated with certain drawbacks that benzyl alcohol, generated by the decomposition of said protecting agent, cannot be easily removed, and that said protecting agent is easily decomposable to significantly generate hydrogen chloride, thus inevitably leading to the decomposition of erythromycin.

In the course of a survey for resolving the drawbacks of such conventional technology, the present inventors have found that a stabler protected des-N-methylerythromycin derivative can be obtained by protecting 2'-hydroxyl and 3'-amino groups with 2-alkenyloxycarbonyl groups and protecting 9-position with a 2-alkenyloxyimino group and that all the protections can be removed in a one-pot reaction under a neutral condition, and thus have reached the present invention.

SUMMARY OF THE INVENTION

The object of the present invention is to provide a protected des-N-methylerythromycin derivative represented by the following formula:

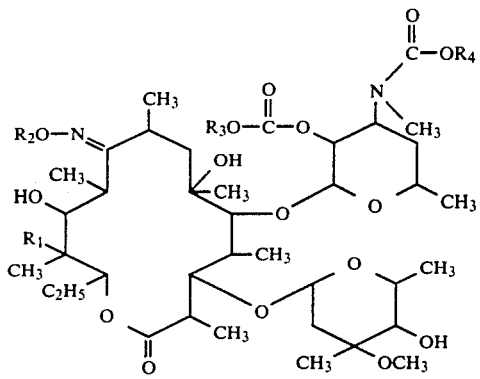

wherein $R_1$ stands for H or OH, and $R_2$, $R_3$ and $R_4$ stand for same or different 2-alkenyl residues such as allyl, methallyl, crotyl, prenyl, 2-pentenyl, 2-ethylbutenyl, cinnamyl, p-chlorocinnamyl, geranyl, neryl, or lower alkoxy-substituted residues thereof.

The number of carbon atoms in said 2-alkenyl group can be suitably selected in consideration of the ease of separation of alkene generated in the removal of protection and the avialability of raw material, but does not usually exceed 10. Particularly in case of a lower alkenyl group with 5 or less carbon atoms, the alkene thus generated can be eliminated from the system in gaseous state.

DETAILED DESCRIPTION OF THE PREFERRED EMBODIMENTS

The process for producing the protected des-N-methylerythromycin derivative of the present invention is not specifically defined, and said derivative can be synthesized for example in the following manner. At first an oxime of erythromycin A or B, as described in Tetrahedron Lett., 157 (1970), is reacted with a 2-alkenylating agent, such as allylbromide, in an aprotic polar solvent such as dimethlformamide and in the presence of a base such as KOH or NaOH to obtain 2-alkenylated oxime. It is then reacted with a 2-alkenyloxycarbonylating agent, such as allyl chloroformate, in a polar solvent such as acetone and in the presence of a base such as sodium bicarbonate to simultaneously achieve 2-alkenyl-oxycarbonylation of 2'-hydroxyl and 3'-tertiary amino groups. The above-mentioned two reactions can also be conducted in the inverted order.

It is also possible to effect 2-alkenyl-oxycarbonylation of 2'-hydroxyl and 3'-amino radicals of erythromycin A or B before forming an oxime, then convert 9-carbonyl radical into an oxime and to thereafter effect 2-alkenylation.

The protected des-N-methylerythromycin derivative thus obtained is useful as an intermediate for synthesizing erythromycin derivatives, in which at least one of 6-, 11- and 4"-hydroxyl groups of erythromycin A or B is alkylated.

Such erythromycin derivatives have superior in vivo activities in comparison with erythromycin A and B, as disclosed in the U.S. Pat. No. 4,331,803, E. Pat. No. 80,819 and U.S. Pat. No. 4,496,717 and can be synthesized, for example, in the following manner.

At first a protected des-N-methylerythromycin derivative is subjected to O-alkylation in usual manner to effect alkylation of said hydroxyl groups. The O-alkylation can be achieved, for example, by a reaction with an alkylating agent such as methyl iodide or ethyl iodide, in a solvent such as dimethyl sulfoxide, tetrahydrofuran and in the presence of a suitable base such as potassium hydroxide.

The O-alkylated compound thus obtained is converted, by the removal of protecting groups in 9-, 2'- and 3'-positions, to a des-N-methylerythromycin derivative. Said removal can be achieved, for example, by heating in dioxane in the presence of palladium acetate, triphenylphosphine and triethyl ammonium formate, and can be conducted quantitatively in a one-pot reaction under a substantially neutral condition.

The des-N-methylerythromycin derivative generated by said removal of protection is then subjected to reductive N-methylation of 3'-sec-amino group in usual manner with formalin, as described in the U.S. Pat. No. 4,331,803, and the oxime at 9-position is converted to a carbonyl radical in usual manner with a reducing agent such as sodium nitritehydrochloric acid or sodium bisulfite, as described in J. Org. Chem., 31, 3446 (1966) to obtain an erythromycin derivative in which hydroxyl groups at 6-, 11- and 4"-positions are suitably alkylated.

In this manner the present invention allows to obtain a compound which is useful as an intermediate for erythromycin derivatives, and which allows removal of protective group in a one-pot reaction under a mild condition.

In the following the present invention will be further clarified by examples and reference examples, in which amounts are represented by parts by weight and percentage by weight, unless otherwise specified.

EXAMPLE

[Allylation]

75 gr. of erythromycin A oxime was dissolved in a mixture of 130 ml. of dried diemthyl sulfoxide and 270 ml. of dried tetrahydrofuran, and cooled with ice. Then 4.43 gr. of 65% oily sodium hydride was added in small portions in a nitrogen atmosphere, and, after agitation for 30 minutes, 14.5 gr. of allyl bromide was added dropwise and agitation was further continued for 2 hours. After the reaction 100 ml. of triethylamine was added and the mixture was agitated for 30 minutes. A major portion of the solvents was distilled off from the reaction mixture, and to the residue was added 1.0 liter of methylene chloride, then washed with saturated aq. solution of sodium chloride and dried over anhydrous magnesium sulfate. 79 gr. of colorless glass-like substance was obtained by distilling off the solvent.

[Allylcarbonation]

2.9 gr. of the above-mentioned glass-like substance, 5.2 gr. of anhydrous potassium carbonate and 10 ml. of acetone were charged in a reactor and agitated under heating at 50° C. Then 4.5 gr. of allyl chloroformate was added dropwise, and the agitation was continued for 3 hours. The reaction mixture was filtered to remove inorganic substance, and the solvent was then distilled off. The residue was dissolved in a small amount of methylene chloride, and dropwise added to a large amount of n-hexane to obtain solid substance. Said solid substance was collected by filtration and recrystallized from isopropanol to obtain 2.2 gr. of 2'-O,N-diallyloxycarbonyl-des-N-methyl-9-allyloxyimino-9-deoxoerythromycin A, having following characteristics:

m.p. 178°–180° C.

elementary analysis (for $C_{47}H_{78}N_2O_{17}$):

theoretical (%): C, 59.85, H, 8.34, N, 2.97, (O, 28.84).

observed (%): C, 59.56, H, 8.25, N, 2.80.

Mass (FAB) m/e=942 (M+). IR (KBr): 3440, 2960, 1750, 1730, 1700, 1640, 990 (cm$^{-1}$).

$^1$H-NMR (400 MHz, CDCl$_3$): δ=2.8., 2.83 (3H), 4.5 (d, 2H), 4.55–4.65 (m, 4H), 5.15–5.35 (m, 6H), 5.85–6.00 (m, 3H).

REFERENCE EXAMPLE 1

[Methylation]

4.9 gr. of allyl carbonate obtained in the foregoing example and 0.96 gr. of methyl iodide were dissolved in a mixture of 30 ml. of dried dimethyl sulfoxide and 40 ml. of dried tetrahydrofuran, and cooled to 0° C. Then under agitation in a nitrogen atmosphere, 0.37 gr. of 95% potassium hydroxide was added, and the agitation was continued for 7 hours. Alter the reaction, 5 ml. of triethyl amine was added, and, after agitation for further 30 minutes, the solvents were distilled off. The residue was dissolved in 100 ml. of methylene chloride, then washed with saturated aq. solution of sodium chloride, and dried over anhydrous magnesium sulfate. By distilling off the solvent, there were obtained 5.0 gr. or crystalline mass containing the 6-O-methylated compound in 80%. The analysis was conducted with HPLC (ODS column: CH$_3$CN—H$_2$O).

REFERENCE EXAMPLE 2

5.0 gr. of the crude 6-O-methylated compound (purity 80%) obtained in the Reference Example 1, 0.037 gr. of palladium acetate, 0.17 gr. of triphenylphosphine, and 7 gr. of triethyl ammonium formate were dissolved in a mixture of 50 ml. of dioxane and 7 ml. of water, and were reacted for 3 hours under reflux. Vigorous gas generation was observed during the reaction. After the distillation of the solvents from the reaction mixture, the residue was dissolved in 100 ml. of diethylether, then washed with saturated aqueous solution of sodium chloride, and dried over anhydrous magnesium sulfate. Crystalline mass obtained by distilling off the solvent were recrystallized from ethanol to obtain 2.90 gr. of 6-O-methyl-des-N-methylerythromycin A oxime, with following characteristics:

m.p.: 247°–249° C.

elementary analysis (for $C_{37}H_{68}N_2O_{13}$):

theoretical (%): C, 59.34, H, 9.15, N, 3.74.

observed (%): C, 59.35, H, 8.87, N, 3.78.

Mass (SIMS) m/s=749 (MH+).

$^1$H-NMR (200 MHz CDCl$_3$): δ=2.41 (3H, s, NCH$_3$), 3.10 (3H, s, 6—OCH$_3$), 3.32 (3H, s, 3"—OCH$_3$).

$^{13}$C-NMR (50.3 MHz, C$_5$D$_5$N): δ=169.2 (C-9), 79.5 (C-6), 51.6 (C$_6$—OCH$_3$), 49.7 (C$_3$"—OCH$_3$), 33.8 (NCH$_3$), 25.8 (C-8) 20.7 (C$_6$—CH$_3$).

What is claimed is:

1. A protected des-N-methylerythromycin derivative represented by a following formula:

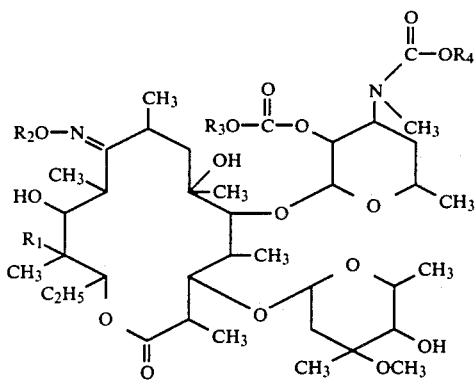

wherein $R_1$ stands for H or OH; and $R_2$, $R_3$ and $R_4$ represent same or different 2-alkenyl groups.

2. A protected des-N-methylerythromycin derivative according to claim 1, wherein $R_2$, $R_3$ and $R_4$ are selected from 2-alkenyl groups each containing 10 or less carbon atoms.

3. A protected des-N-methylerythromycin derivative according to claim 2, wherein $R_2$, $R_3$ and $R_4$ are selected from 2-alkenyl groups each containing 5 or less carbon atoms.

4. A protected des-N-methylerythromycin derivative according to claim 3, wherein said 2-alkenyl group is selected from a group consisting of allyl, methallyl, crotyl, prenyl and 2-pentenyl radicals.

5. A protected des-N-methylerythromycin derivative according to claim 1, wherein $R_1$ is an OH radical.

* * * * *